United States Patent [19]

Kleker

[11] 4,076,419
[45] Feb. 28, 1978

[54] METHOD AND APPARATUS FOR HEMATOLOGY

[76] Inventor: Richard G. Kleker, 242 25th St., Richmond, Calif. 94804

[21] Appl. No.: 704,429

[22] Filed: Jul. 12, 1976

[51] Int. Cl.² .................... G01N 33/16; G01F 17/00; C09K 3/00
[52] U.S. Cl. .................. 356/39; 23/230 B; 73/149; 252/408; 324/71 CP; 424/2
[58] Field of Search .................... 356/39–42, 356/102, 207–208; 73/149; 252/408; 324/71 CP; 23/230 B; 235/92 PC; 250/222 PC; 128/2 G; 424/2

[56] References Cited

U.S. PATENT DOCUMENTS

| 3,558,522 | 1/1971 | Louderback et al. | 252/408 |
| 3,977,995 | 8/1976 | Louderback et al. | 23/230 B |
| 3,997,838 | 12/1976 | Shamos et al. | 324/71 CP |

OTHER PUBLICATIONS

McFadyen et al. "An Automatic Flow Ultramicroscope For Submicron Particle Counting & Size Analysis" Jr. of Colloid & Interface Science, 12-1973, pp. 573–583.
Seiverd, C. E. "Hematology for Medical Technologists" Lea & Febiger, 1975, pp. 77–81.
Volemetron, Advertisement From Atomium 900 Main St., Waltham, Mass.

Primary Examiner—John K. Corbin
Assistant Examiner—Wm. H. Punter
Attorney, Agent, or Firm—Lothrop & West

[57] ABSTRACT

A predetermined number of small latex beads is provided in the vacuum capsule of a Vacutainer. After blood is drawn into the capsule, the capsule is agitated to mix the blood and beads into a homogeneous suspension. A smear or spun slide is prepared of the suspension for microscopic analysis. The beads in the microscope field are counted in addition to the white blood cells, thereby enabling calculation of the volume of blood in the microscope field to provide an absolute white cell count. Absolute red cell, platelet and differential white cell counts are obtained in the same manner. The beads have a predetermined uniform size and color density thereby enabling cell size and hemoglobin percentage measurements.

6 Claims, 4 Drawing Figures

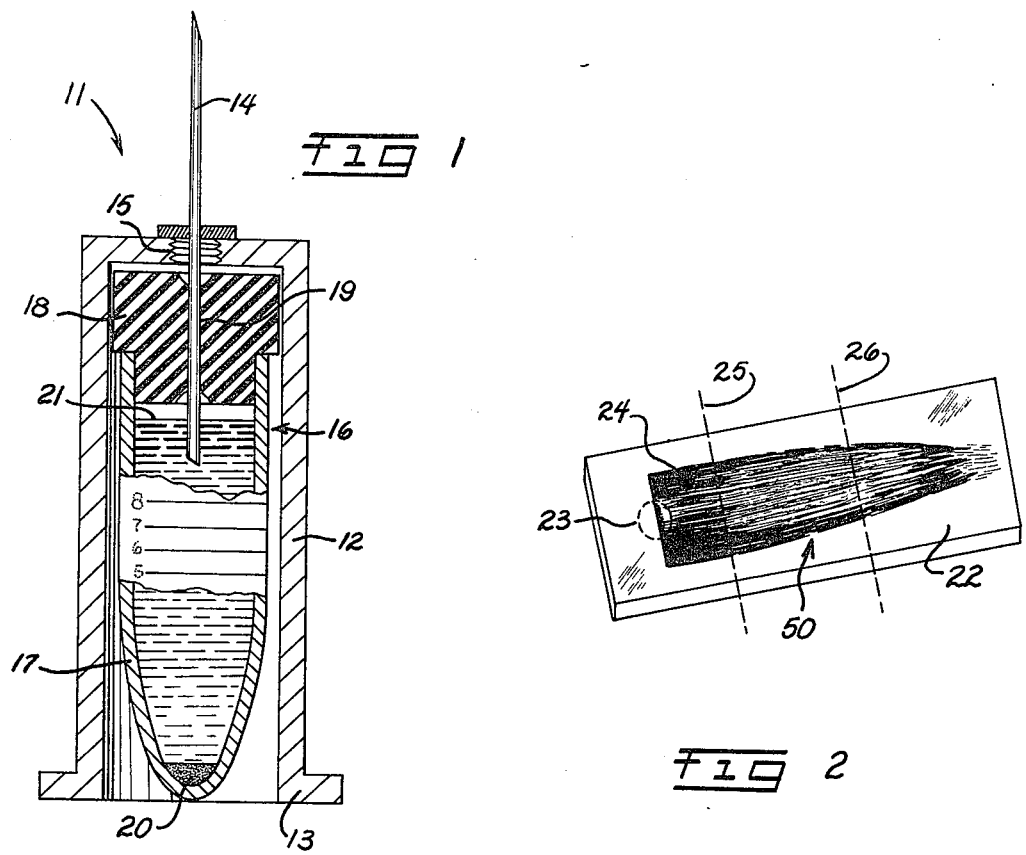
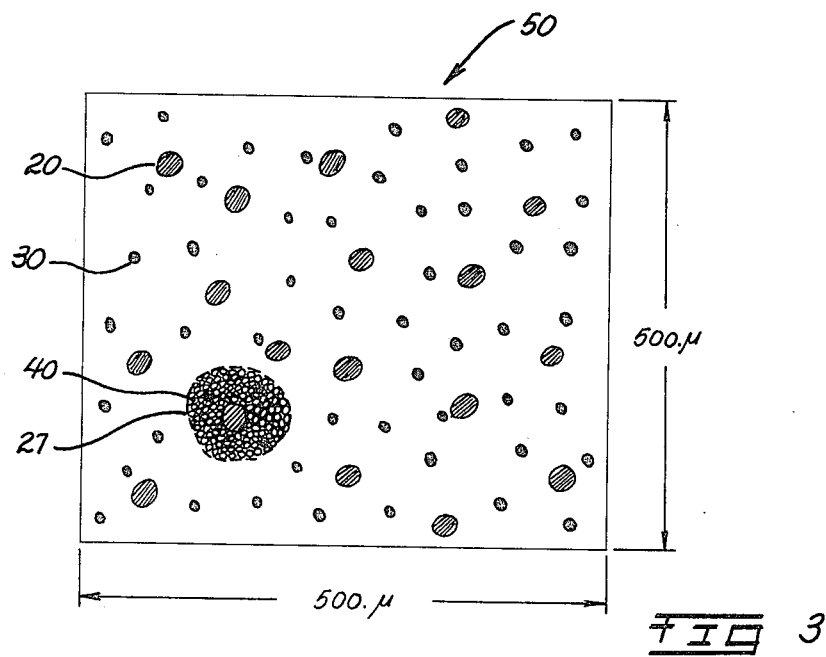

METHOD AND APPARATUS FOR HEMATOLOGY

BACKGROUND OF THE INVENTION

Hematology testing is generally performed utilizing two distinct methodologies; cell blood count which enumerates the white cell, red cell and platelet counts; and differential blood count which enumerates the percentages of the types of white cells. Cell blood count is currently being performed in large institutions by automatic electronic instruments such as the popular "Coulter Electronic Blood Cell Counter." Although electronic instruments are under development for determination of the differential blood count by means of image recognition, the technology is complex and the instruments will be necessarily expensive. At the present time, no instrument is commercially available which provides both cell blood count and differential blood count.

For these reasons, differential blood count is still obtained by the traditional method of microscopy. A smear or spun slide is prepared of the patient's blood and at least 200 white cells are manually counted by means of microscopic magnification and classified as to type to determine the percentages of the white cell types in the blood. Since the volume of blood in the microscope field is not known, microscopy to date has not been able to provide absolute cell counts. If it is desired to know the absolute numbers of white cell types in the blood, the percentages derived from the differential blood count must be multiplied by the absolute white cell count derived from the cell blood count.

The electronic instruments utilized in hematology are too expensive for small institutions. Individual physicians and small clinics must rely on specialized laboratories for hematological analysis, and the delay in transporting blood samples to and from the laboratories is sometimes fatal in emergency cases. Another disadvantage of the electronic instruments is that they often malfunction, and must be carefully checked and calibrated on a daily basis.

The admixture of latex beads with blood constituents in itself is not new. A specific application is disclosed in U.S. Pat. No. 3,558,522 in which washed red blood cells and latex beads are mixed together in a fluid suspension to provide a calibration standard for electronic cell blood count instruments. The latex beads replace the white blood cells which are removed by the washing process.

Latex beads are used in the present invention in a completely different and novel manner to enable absolute blood counts to be performed by microscopy, thereby enabling cell blood count and differential blood count analysis to be performed by any person skilled in the art from a single blood sample in a short period of time.

SUMMARY OF THE INVENTION

The present invention relates to a method and apparatus for hematology testing. Simply stated, the present invention provides a predetermined number of small latex beads in the capsule of a conventional Vacutainer. After a patient's blood is drawn into the capsule, the capsule is agitated to provide a homogeneous suspension. A smear or spun slide is prepared of the suspension for microscopic analysis. In addition to the number of blood cells in the microscope field, the latex beads in the field are also counted to enable calculation of the volume of blood appearing in the field, thereby enabling absolute cell blood counts.

It is an object of the invention to provide a method and apparatus for hematology testing which enables both cell blood count and differential blood count to be obtained microscopically from a single blood sample.

It is another object of the invention to permit adding a cell blood count evaluation to a permanent slide specimen, thereby providing an expanded review capacity beneficial in teaching and helpful in difficult chronic diagnosis situations.

It is another object of the invention to provide a low cost method of checking the accuracy of electronic cell blood count instruments.

It is another object of the invention to provide a method of obtaining accurate absolute platelet counts.

It is still another object of the invention to provide a method by which an entire blood analysis may be performed from a quantity as small as one or two drops of whole blood, which is of especial benefit in specimen collection from infants and elderly patients.

It is yet another object of the invention to provide a generally improved method and apparatus for hematology.

Other objects, together with the foregoing, are attained in the embodiment described in the following description and illustrated in the accompanying drawings.

BRIEF DESCRIPTION OF THE DRAWING

FIG. 1 is a front elevational view of an improved blood drawing instrument embodying the present invention, with portions of the device being shown in median longitudinal section;

FIG. 2 is a perspective view of a blood smear slide;

FIG. 3 is a view to an enlarged scale illustrating a microscopic magnification of a usable area of the slide shown in FIG. 2; and, FIG. 4 is a flow chart illustrating the method of the present invention.

DESCRIPTION OF THE PREFERRED EMBODIMENT

Figure 4:
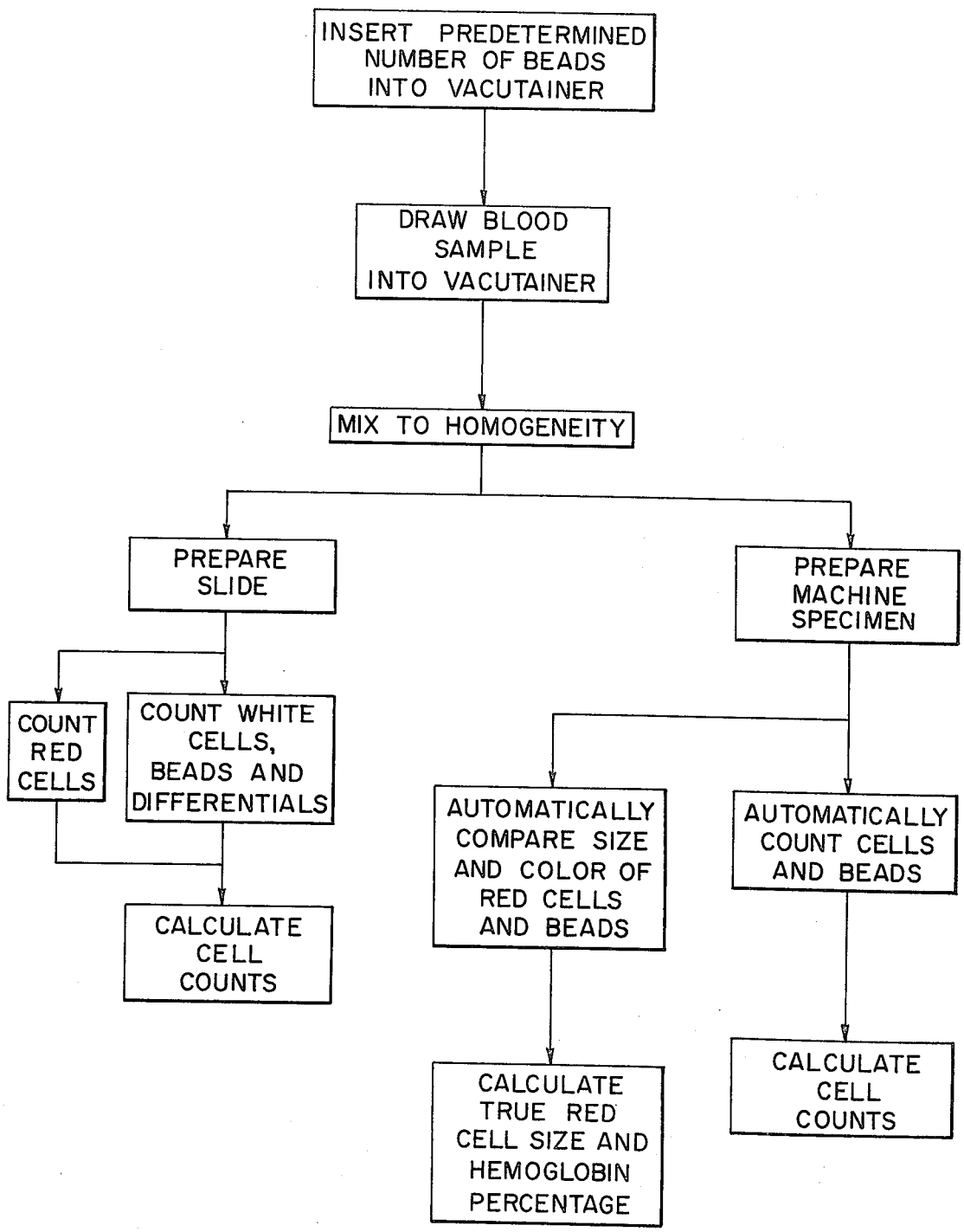

While the invention is susceptible of numerous physical embodiments, depending upon the environment and requirements of use, substantial numbers of the herein shown and described embodiment have been made, tested and used, and all have performed in an eminently satisfactory manner.

With particular reference to FIG. 1 of the drawing, an improved blood drawing instrument used in connection with practicing the method of the present invention is generally designated by the reference numeral 11 and comprises a tubular support 12, or body, provided at its lower end, as viewed in FIG. 1, with an enlarged lip 13, or flange. A hollow needle 14 including a threaded base fitting is screwed into a threaded opening 15 in the upper end of the tubular body 12, as viewed in FIG. 1, so as partially to extend downwardly into the body chamber.

The instrument 11 further comprises an evacuated container 16, or capsule, comprising a transparent tube 17 closed at its bottom end, as viewed in FIG. 1. The upper end of the capsule 16 is closed by a resilient plug 18, or stopper, formed of plastic or the like. A central hole 19 is axially pierced through the plug 18 extending from the interior of the plug 18 externally upwardly thereof. Owing to the resiliency of the plug material, the hole 19 is normally closed.

The instrument 11 described thus far is known in the art as a "Vacutainer" and is in widespread popular use in a great number of medical institutions. To use the instrument 11, a needle cover is removed and the needle 14 previously fitted on the body 12, is inserted into the patient's vein. The capsule 16 is then inserted into the tubular chamber of the body 12, with the lip 13 providing leverage for the fingers of the practitioner, until the inner end of the needle 14 intrudes into the interior of the capsule 16 through the hole 19 in the plug 18, thereby establishing communication between the interior of the capsule 16 and the patient's vein through the needle 14.

Since air in the capsule 16 is evacuated during manufacture, blood is quickly sucked into the capsule 16 until the pressure in the capsule 16 is raised to that in the vein, thereby substantially filling the capsule 16. The entire instrument 11 is thereupon detached from the patient, and the capsule 16 subsequently removed from the body 12 for analysis of the blood sample contained therein.

The instrument 11 differs from a conventional Vacutainer in that a predetermined number of particles or beads 20 is inserted in the capsule 16 during manufacture. The beads 20 are made of latex or other suitable inert material and preferably are substantially perfect spheres of uniform size and predetermined color. The diameter of each bead 20 is in the same range, or order of magnitude, as the white and red blood cells, or between 2 and 20 microns. The number of beads 20 is selected so as to approximate a normal white blood cell count, or between 5,000 and 10,000 per cubic millimeter of blood in the capsule 16.

As is also shown in FIG. 1, the capsule 16 is provided with suitable graduations so that when the instrument 11 is held vertically, the practitioner may determine the volume of blood drawn into the capsule 16 by comparing the position of the surface 21 of the blood with the graduations.

FIG. 2 illustrates the preparation of a smear slide from the blood sample in the capsule 16. The capsule 16 is first shaken or otherwise agitated to provide a homogeneous suspension of the beads 20 in the blood. A small amount of the blood is then withdrawn from the capsule 16 by removing the stopper 18 and introducing a capillary tube into the blood sample. A drop of the blood from the capillary tube is placed on a glass plate or slide 22 at a position indicated by a phantom circle 23. The edge of another slide (not shown) is used to smear the drop in a right hand direction to form a smear 24. The area of the smear 24 to the left of a transverse phantom line 25 is not suitable for microscopic analysis because it is too thick; i.e. the blood cells overlap and are difficult to count. The area of the smear 24 to the right of a transverse phantom line 26 is also not suitable since it is too thin; the entire area is not covered with cells. The area of the smear 24 suitable for analysis is between the lines 25 and 26 in which the thickness is substantially equal to that of one blood cell.

A portion of the smear 24 between the lines 25 and 26, typically a 500 micron square examination area, generally designated by the reference numeral 50, is manually examined through microscopic magnification. The appearance of the microscope field 50 is shown in FIG. 3 in which the large hatched particles are the latex beads 20 and the dark spheres 30 are white blood cells which are preferably selectively stained blue in a conventional manner to make them easily visible and distinguishable from the other blood constituents. In an area enclosed by a phantom circle 27, the red blood cells 40 are shown as open circles. The platelets are not shown for simplicity of illustration.

To obtain an absolute white blood cell count, the stained, or colored, white blood cells 30 and the latex beads 20 in the examination area 50 are both counted. The predetermined original number of latex beads 20 and the original volume of blood in the capsule 16 are both known.

It is also known that in a homogeneous mixture, the ratio of the number of beads 20 counted in the examination area 50 to the predetermined original number of beads equals the ratio of the volume of blood in the examination area to the original volume of blood in the capsule 16. So also, the ratio of the number of white cells 30 counted in the examination area 50 to the unknown total number of white cells in the original volume of blood equals the ratio of the volume of blood in the examination area to the original volume of blood in the capsule 16.

These ratios enable the practitioner to calculate the number of white blood cells per unit volume from the counted number of white blood cells and beads in the examination area. A formula which can be utilized for this calculation is as follows:

$$\text{No. of white cells per unit volume} = \frac{\text{white cell count}}{\text{bead count}} \times \frac{\text{predetermined original no. of beads}}{\text{original volume of blood}}$$

EXAMPLE

| | |
|---|---|
| Counted no. of white cells in examination area | 25 |
| Counted no. of beads in examination area | 20 |
| Predetermined original no. of beads | $75 \times 10^6$ |
| Original volume of blood in capsule | $10 \times 10^3$ mm$^3$ |

$$\text{No. of white cells per mm}^3 = \frac{25}{20} \times \frac{75 \times 10^6}{10 \times 10^3} = 9375$$

The volume of blood in the examination area 50 is 0.0027 mm$^3$. It can therefore be seen that an accurate absolute blood count can be obtained from a very small quantity of blood, a capability which is most advantageous when collecting specimens from infants and elderly patients.

The differential blood count is obtained in the same manner by counting the white cells of each type in the examination area. Red cell counts and platelet counts may also be taken if required, although these counts are somewhat more time consuming due to the relatively larger numbers of red cells 40 and platelets (not shown) in the blood.

The uniform size of the beads 20 enables accurate size comparisons to be made between the beads 20 and the blood cells to determine the actual cell sizes. Also, the hemoglobin percentage may be determined by comparing the colors of the red cells and the beads 20.

As illustrated in the flow chart of FIG. 4, the blood sample in the capsule 16 may be used to prepare a machine specimen for an electronic blood testing instrument of the type described using an image recognition process. Such an instrument in combination with the present beads 20 is capable of automatically performing both the blood cell count operations with increased accuracy using the beads 20 as standards and the size and color (or monochromatic density) comparisons described above.

It should be noted, at this juncture, that if the density of the colored latex beads 20 is adequate for observation by an instrument, the same specimen could be used either manually or automatically.

It will be seen that the present invention places accurate blood counts within the reach of all practitioners by improving the traditional technique of microscopy of smear or spun slide specimens. The savings in expense and timeliness provided by the invention are a substantial contribution to the medical field.

What is claimed is:

1. A method of hematology testing comprising the steps of:
   a. mixing to homogeneity a predetermined volume of blood and a predetermined number of particles;
   b. smearing a small amount of the mixture onto a plate;
   c. counting the white cells of the blood and particles respectively on a predetermined area of the plate; and,
   d. multiplying a ratio of the counted number of white cells to the counted number of particles by a ratio of said predetermined number of particles to said predetermined volume of blood to determine a number of white cells per unit volume of the blood.

2. A method as in claim 1 further comprising the steps of:
   e. counting the red cells of the blood on said predetermined area of the plate; and,
   f. multiplying a ratio of the counted number of red cells to said counted number of particles by the ratio of said predetermined number of particles to said predetermined volume of blood to determine a number of red cells per unit volume of the blood.

3. A method as in claim 2 in which said particles have a predetermined size, the method further comprising the step of:
   g. comparing the size of the red blood cells to said predetermined size of said particles.

4. A method as in claim 2 in which said particles have a predetermined color, the method further comprising the step of:
   h. comparing the color of the red blood cells to said predetermined color of said particles.

5. A method as in claim 1 further comprising the steps prior to step (a), of:
   i. providing the predetermined number of particles in an evacuated container; and,
   j. drawing the blood into the evacuated container by means of the vacuum therein; step (a) comprising agitating the container.

6. A method as in claim 5 in which the container is provided with graduations, the method further comprising the steps, between steps (j) and (b), of:
   k. orienting the container so that the surface of the blood in the container is aligned with the graduations; and,
   l. comparing the position of the surface of the blood in the container with the graduations to determine the predetermined volume of blood.

* * * * *